(12) United States Patent
Mihan et al.

(10) Patent No.: US 6,858,688 B2
(45) Date of Patent: Feb. 22, 2005

(54) AMINO ACID COMPLEXES AND THE USE THEREOF IN PRODUCING OLEFIN POLYMERS

(75) Inventors: Shahram Mihan, Ludwigshafen (DE); Wolfgang Beck, Munich (DE); Walter Ponikwar, Munich (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/380,475

(22) PCT Filed: Sep. 19, 2001

(86) PCT No.: PCT/EP01/10804

§ 371 (c)(1),
(2), (4) Date: Mar. 20, 2003

(87) PCT Pub. No.: WO02/24330

PCT Pub. Date: Mar. 28, 2002

(65) Prior Publication Data

US 2004/0024150 A1 Feb. 5, 2004

(30) Foreign Application Priority Data

Sep. 21, 2000  (DE) .......................................... 100 47 461

(51) Int. Cl.$^7$ ................................................ C08F 4/42
(52) U.S. Cl. ....................... 526/161; 526/348; 502/103; 502/162
(58) Field of Search ................................ 526/348, 161; 502/103, 162

(56) References Cited

U.S. PATENT DOCUMENTS

| | | | | |
|---|---|---|---|---|
| 2,380,474 | A | * 7/1945 | Stewart | 526/213 |
| 3,454,680 | A | * 7/1969 | Okuya et al. | 526/86 |
| 5,834,393 | A | * 11/1998 | Jacobsen et al. | 502/152 |
| 6,069,253 | A | 5/2000 | Chaudhari et al. | |

FOREIGN PATENT DOCUMENTS

| | | |
|---|---|---|
| EP | 0 579 900 | 12/1997 |
| EP | 0 576 970 | 1/1998 |
| JP | 50-101304 | * 8/1975 |
| WO | 96/23010 | 8/1996 |
| WO | 98/27124 | 6/1998 |

OTHER PUBLICATIONS

Sheldrick et al., Journal of Organometallic Chemistry, 467, 283–292 (1994).*
Erickson et al., Inorganic Chemistry, 36, 284–290(1997).*
Hieber et al., Z. anorg. allg. Chem., 377, 235–240(1970).*
Carmona et al., Chem. Eur. J. 5(5), 1544–1564(1999).*
Milos I. Djuran et al.: "Hydrolysis of amide bond in histidine–containing peptides promoted by chelated amino acid palladium(II) complexes: dependence of hydrolytic pathway on the coordination modes of the peptides" Polyhedron, vol. 18, No. 27, pp. 3611–3616, 1999.

Database CA 'Online! Chemical Abstracts Service, Columbus, OH, US Database accession No. 82:154788 XP002192432.

Database CA 'Online! Chemical Abstracts Service, Columbus, OH, US Database accession No. 121:194283, XP002192433.

Database CA 'Online! Chemical Abstracts Service, Columbus, OH, US Database accession No. 131:88027, XP002192434.

Database CA 'Online! Chemical Abstracts Service, Columbus, OH, US Database accession No. 126:131591, XP00219435.

Trevor G. Appleton et al.: "Di–and trimethylplatinum(IV) complexes with aspartate: some subtle effects of chelate ring size" Polyhedron, vol. 14, No. 19, pp. 2613–2622, 1995.

Database CA 'Online! Chemical Abstracts Service, Columbus, OH, US Database accession No. 123:131033, XP002192436.

Database CA 'Online! Chemical Abstracts Service, Columbus, OH, US Database accession No. 123:245452, XP002192437.

Database CA 'Online! Chemical Abstracts Service, Columbus, OH, US Database accession No. 121:35813, XP002192438.

Database CA 'Online! Chemical Abstracts Service, Columbus, OH, US Database accession No. 112:47551, XP002192439.

Database CA 'Online! Chemical Abstracts Service, Columbus, OH, US Database accession No. 104:236044, XP002192440.

Database CA 'Online! Chemical Abstracts Service, Columbus, OH, US Database accession No. 89:31695, XP002192441.

(List continued on next page.)

Primary Examiner—Ling-Siu Choi
(74) Attorney, Agent, or Firm—Oblon, Spivak, McClelland, Maier & Neustadt, P.C.

(57) ABSTRACT

An amino acid complex of the formula I,

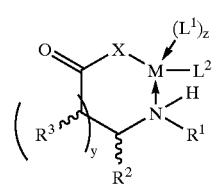

I where M is selected from among Fe, Co, Ni, Pd, Pt and Ir, preferably Ni, can be used for the polymerization of olefins.

17 Claims, No Drawings

OTHER PUBLICATIONS

Database CA 'Online! Chemical Abstracts Service, Columbus, OH, US Database accession No. 73:70377, XP002192442.

Database CA 'Online! Chemical Abstracts Service, Columbus, OH, US Database accession No. 74:134275, XP002192475.

Hans H. Brintzinger et al.: "Stereospecific olefin polyerization with chiral metallocene catalysts" Angew. Chem. Int. Ed. Engl., vol. 34, pp. 1143–1170 1995.

Kay Severin et al.: "Synthese und kristallstruktur von Rh(I)–komplexen mit alpha–aminocaroxylat–liganden" Chem. Ber., vol. 128, pp. 1127–1130, 1995.

* cited by examiner

AMINO ACID COMPLEXES AND THE USE THEREOF IN PRODUCING OLEFIN POLYMERS

BACKGROUND OF THE INVENTION

1. Field of the Invention

The present invention relates to amino acid complexes of the formula I,
where the variables are defined as follows:

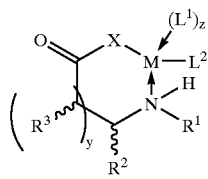

M is selected from among Fe, Co, Ni, Pd, Pt and Ir,
X is selected from among O and S;
$R^1$ and $R^2$ are identical or different and are each selected from among
  hydrogen,
  $C_1$–$C_8$-alkyl, substituted or unsubstituted,
  $C_3$–$C_{12}$-cycloalkyl, substituted or unsubstituted,
  $C_7$–$C_{13}$-aralkyl,
  $C_6$–$C_{14}$-aryl, unsubstituted or substituted by one or more identical or different substituents selected from among
    $C_1$–$C_8$-alkyl, substituted or unsubstituted,
    $C_3$–$C_{12}$-cycloalkyl,
    $C_7$–$C_{13}$-aralkyl,
    $C_6$–$C_{14}$-aryl,
    halogen,
    $C_1$–$C_6$-alkoxy,
    $C_6$–$C_{14}$-aryloxy,
    $SiR^4R^5R^6$ and O—$SiR^4R^5R^6$, where $R^4$–$R^6$ are selected from among $C_1$–$C_8$-alkyl, $C_3$–$C_{12}$-cycloalkyl, $C_7$–$C_{13}$-aralkyl and $C_6$–$C_{14}$-aryl;
  five- to six-membered nitrogen-containing heteroaryl radicals Y, unsubstituted or substituted by one or more identical or different substituents selected from among
    $C_1$–$C_8$-alkyl, substituted or unsubstituted,
    $C_3$–$C_{12}$-cycloalkyl,
    $C_7$–$C_{13}$-aralkyl,
    $C_6$–$C_{14}$-aryl,
    halogen,
    $C_1$–$C_6$-alkoxy,
    $C_6$–$C_{14}$-aryloxy,
    $SiR^4R^5R^6$ and O—$SiR^4R^5R^6$, where $R^4$–$R^6$ are selected from among $C_1$–$C_8$-alkyl, $C_3$–$C_{12}$-cycloalkyl, $C_7$–$C_{13}$-aralkyl and $C_6$–$C_{14}$-aryl,
  and $CH_2$—Y, where Y is as defined above;
y is an integer from 0 to 4;
$L^1$ is an uncharged, inorganic or organic ligand;
$L^2$ is an inorganic or organic anionic ligand, where $L^1$ and $L^2$ may be joined to one another by one or more covalent bonds;
z is an integer from 0 to 3;
x is an integer from 0 to 3.

Furthermore, the present invention relates to a process for preparing the novel amino acid complexes of the formula I and to catalyst systems for the polymerization or copolymerization of olefins, comprising one or more amino acid complexes of the formula I and, if desired, an activator, and also to a process for the polymerization or copolymerization of olefins using the catalyst system of the present invention.

2. Description of the Background

Polymers and copolymers of olefins are of great economic importance because the monomers are readily available in large quantities and because the polymers can be varied within a wide range by variation of the production process or the processing parameters. In the production process, particular attention has to be paid to the catalyst used.

The systems described in the literature are not free of disadvantages. Thus, the cyclopentadienyl ligands of most metallocenes require complicated syntheses which can take 4 or more hours, for example as described in H.-H. Brintzinger et al., Angew. Chem. 1995, 107, 1255, in EP-A 0 549 900 or EP-A 0 576 970. However, multistage syntheses make the catalysts more expensive.

The systems disclosed in WO 96/23010 give, after activation with methylaluminoxane ("MAO"), highly branched polymers which, however, do not have a sufficiently high molecular weight for numerous materials applications.

The complexes described by Brookhart and Gibson (e.g. WO 98/27124) are simple to obtain in terms of the synthesis, but they only incorporate comonomers in very small amounts. The polymerization of ethylene, for example, gives highly linear, brittle polymers having a limited suitability as materials. K. Severin et al., Chem. Ber. 1995, 128, 1127, disclose Rh complexes of the formula A

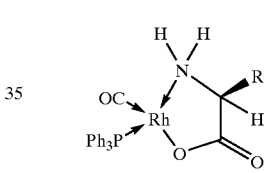

where R=methyl or benzyl, which can readily be synthesized from the natural amino acids. They are suitable as chiral catalysts for hydrogenation, as cytostatics or as labeling reagents in biochemistry. However, they are unsuitable as polymerization catalysts.

SUMMARY OF THE INVENTION

It is an object of the present invention to provide
novel complexes which are polymerization-active toward olefins, whose ligands can be obtained by simple syntheses or are commercially available and which give high molecular weight polyethylene;
catalyst systems for the polymerization or copolymerization of olefins, comprising the novel complexes and suitable activators,
a process for the polymerization or copolymerization of olefins using these catalyst systems,
a process for preparing the complexes,
a solid catalyst which is suitable for gas-phase polymerization, suspension polymerization or bulk polymerization and comprises a complex, a suitable activator and a solid support,
a process for preparing a solid catalyst from the novel complexes, and
to use these for the polymerization or copolymerization of olefins.

DETAILED DESCRIPTION OF THE PREFERRED EMBODIMENTS

We have found that this object is achieved by the amino acid complexes defined at the outset.

In formula I

M is selected from among elements of groups 6 to 10 of the Periodic Table of the Elements, for example Fe, Co, Ni, Pd, Pt or Ir, preferably Ni or Pd and particularly preferably Ni;

X is selected from among oxygen and sulfur; preference is given to oxygen;

$R^1$ to $R^3$ are identical or different and are selected from among hydrogen;

$C_1$–$C_8$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_8$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_1$–$C_8$-alkyl groups substituted by one or more functional groups such as amino groups, hydroxyl groups, thioether groups, thiol groups, carboxyl groups or guanidine groups; particular preference is given to the following functionalized alkyl groups:

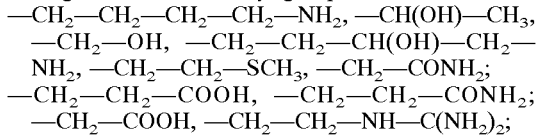

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

examples of substituted cycloalkyl groups are: 2-methylcyclopentyl, 3-methylcyclopentyl, cis-2,4-dimethylcyclopentyl, trans-2,4-dimethylcyclopentyl, cis-2,5-dimethylcyclopentyl, trans-2,5-dimethylcyclopentyl, 2,2,5,5-tetramethylcyclopentyl, 2-methylcyclohexyl, 3-methylcyclohexyl, 4-methylcyclohexyl, cis-2,6-dimethylcyclohexyl, trans-2,6-dimethylcyclohexyl, cis-2,6-diisopropylcyclohexyl, trans-2,6-diisopropylcyclohexyl, 2,2,6,6-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,6,6-tetrachlorocyclohexyl, 2-thiomethylcyclopentyl, 2-thiomethylcyclohexyl, 3-thiomethylcyclopentyl, 3-thiomethylcyclohexyl and further derivatives;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

$C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl substituted by one or more identical or different substituents selected from among $C_1$–$C_8$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_8$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

halogen, for example fluorine, chlorine, bromine and iodine, particularly preferably fluorine and chlorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

silyl groups $SiR^4R^5R^6$, where $R^4$–$R^6$ are selected independently from among hydrogen, $C_1$–$C_8$-alkyl groups, the benzyl group and $C_6$–$C_{14}$-aryl group; preference is given to the trimethylsilyl, triethylsilyl, triisopropylsilyl, diethylisopropylsilyl, dimethylhexylsilyl, tert-butyldimethylsilyl, tert-butyldiphenylsilyl, tribenzylsilyl, triphenylsilyl and tri-para-xylylsilyl groups; particular preference is given to the trimethylsilyl group and the tert-butyldimethylsilyl group;

silyloxy groups O—SiR$^4$R$^5$R$^6$, where R$^4$–R$^6$ are selected independently from among hydrogen, $C_1$–$C_8$-alkyl groups, the benzyl group and $C_6$–$C_{14}$-aryl group; preference is given to the trimethylsilyloxy, triethylsilyloxy, triisopropylsilyloxy, diethylisopropylsilyloxy, dimethylhexylsilyloxy, tert-butyldimethylsilyloxy, tert-butyldiphenylsilyloxy, tribenzylsilyloxy, triphenylsilyloxy and tri-para-xylylsilyloxy groups; particular preference is given to the trimethylsilyloxy group and the tert-butyldimethylsilyloxy group;

five- to six-membered nitrogen-containing heteroaryl radicals such as N-pyrrolyl, pyrrol-2-yl, pyrrol-3-yl, N-imidazolyl, 2-imidazolyl, 4-imidazolyl, 5-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl, 2-indolyl, 3-indolyl and N-carbazolyl;

five- to six-membered nitrogen-containing heteroaryl radicals such as N-pyrrolyl, pyrrol-2-yl, pyrrol-3-yl, N-imidazolyl, 2-imidazolyl, 4-imidazolyl, 5-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl, 2-indolyl, 3-indolyl and N-carbazolyl substituted by one or more identical or different substituents selected from among $C_1$–$C_8$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_8$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

halogen, for example fluorine, chlorine, bromine and iodine, particularly preferably fluorine and chlorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

silyl groups SiR$^4$R$^5$R$^6$, where R$^4$–R$^6$ are selected independently from among hydrogen, $C_1$–$C_8$-alkyl groups, the benzyl group and $C_6$–$C_{14}$-aryl group; preference is given to the trimethylsilyl, triethylsilyl, triisopropylsilyl, diethylisopropylsilyl, dimethylhexylsilyl, tert-butyldimethylsilyl, tert-butyldiphenylsilyl, tribenzylsilyl, triphenylsilyl and tri-para-xylylsilyl groups; particular preference is given to the trimethylsilyl group and the tert-butyldimethylsilyl group;

silyloxy groups O—SiR$^4$R$^5$R$^6$, where R$^4$–R$^6$ are selected independently from among hydrogen, $C_1$–$C_8$-alkyl groups, the benzyl group and $C_6$–$C_{14}$-aryl group; preference is given to the trimethylsilyloxy, triethylsilyloxy, triisopropylsilyloxy, diethylisopropylsilyloxy, dimethylhexylsilyloxy, tert-butyldimethylsilyloxy, tert-butyldiphenylsilyloxy, tribenzylsilyloxy, triphenylsilyloxy and tri-para-xylylsilyloxy groups; particular preference is given to the trimethylsilyloxy group and the tert-butyldimethylsilyloxy group;

or R$^1$ to R$^3$ may be $C_1$–$C_8$-alkyl substituted by a 5- to 6-membered heteroaromatic Y, preferably methyl substituted by a 5- to 6-membered heteroaromatic, for example 3-indolylmethyl or 5-imidazolylmethyl.

In a preferred embodiment, two adjacent radicals R$^1$ to R$^3$ are covalently bound to one another and form a 5- to 10-membered ring. Thus, for example, R$^1$ and R$^2$ may together be: —(CH$_2$)$_3$-(trimethylene), —(CH$_2$)$_4$-(tetramethylene), —(CH$_2$)$_5$-(pentamethylene), —(CH$_2$)$_6$-(hexamethylene), —CH$_2$—CH═CH—, —CH$_2$—CH═CH—CH$_2$—, —CH═CH—CH═CH—, —O—CH$_2$—O—, —O—CHMe—O—, —O—CH—(C$_6$H$_5$)—O—, —O—CH$_2$—CH$_2$—O—, —O—CMe$_2$—O—, —NMe—CH$_2$—CH$_2$—NMe—, —NMe—CH$_2$—NMe— or —O—SiMe$_2$—O— where Me═CH$_3$. In a preferred example, R$^1$ and R$^2$ together form a trimethylene unit which may in turn bear one or more $C_1$–$C_8$-alkyl or hydroxyl groups as substituents, where $C_1$–$C_8$-alkyl is as defined above.

y is an integer from 0 to 4, particularly preferably 0.

L$^1$ are identical or different and are selected from among uncharged, inorganic or organic ligands, for example from among phosphines of the formula (R$^7$)$_x$PH$_{3-x}$ and amines of the formula (R$^7$)$_x$NH$_{3-x}$, where x is an integer from 0 to 3. However, ethers (R$^7$)$_2$O such as dialkyl ethers, e.g. diethyl ether, or cyclic ethers, for example tetrahydrofuran, H$_2$O, alcohols (R$^7$)OH such as methanol or ethanol, pyridine, pyridine derivatives of the formula C$_5$H$_{5-x}$(R$^7$)$_x$N, for example 2-picoline, 3-picoline, 4-picoline, 2,3-lutidine, 2,4-lutidine, 2,5-lutidine, 2,6- lutidine or 3,5-lutidine, CO, $C_1$–$C_{12}$-alkyl nitriles or $C_6$–$C_{14}$-aryl nitriles, e.g. acetonitrile, propionitrile, butyronitrile or benzonitrile, are also suitable. Further ligands which can be employed are singly or multiply ethylenically unsaturated double bond systems such as ethenyl, propenyl, cis-2-butenyl, trans-2-butenyl, cyclohexenyl or norbornenyl.

$L^2$ is selected from among inorganic and organic anionic ligands, for example from among halide ions such as fluoride, chloride, bromide and iodide, preferably chloride and bromide, amide anions $(R^7)_h NH_{2-h}$, where h is an integer from 0 to 2, $C_1$–$C_6$-alkyl anions such as $(CH_3)^-$, $(C_2H_5)^-$, $(C_3H_7)^-$, $(n\text{-}C^4H_9)^-$, $(^{tert\text{-}C}{_4}H_9)^-$ and $(C_6H_{14})^-$;

the allyl anion and the methallyl anion, the benzyl anion and $C_6$–$C_{14}$-aryl anions such as $(C_6H_5)^-$.

Here, the radicals $R^7$ are identical or different and are selected independently from among hydrogen, $C_1$–$C_8$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

the benzyl group and $C_6$–$C_{14}$-aryl groups, such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

$C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl substituted by one or more identical or different substituents selected from among $C_1$–$C_8$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_8$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

halogen, such as fluorine, chlorine, bromine and iodine, particularly preferably fluorine and chlorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

silyl groups $SiR^4R^5R^6$, where $R^4$–$R^6$ are selected independently from among hydrogen, $C_1$–$C_8$-alkyl groups, the benzyl group and $C_6$–$C_{14}$-aryl group; preference is given to the trimethylsilyl, triethylsilyl, triisopropylsilyl, diethylisopropylsilyl, dimethylhexylsilyl, tert-butyldimethylsilyl, tert-butyldiphenylsilyl, tribenzylsilyl, triphenylsilyl and tri-para-xylylsilyl groups; particular preference is given to the trimethylsilyl group and the tert-butyldimethylsilyl group;

silyloxy groups O—$SiR^4R^5R^6$, where $R^4$–$R^6$ are selected independently from among hydrogen, $C_1$–$C_8$-alkyl groups, the benzyl group and $C_6$–$C_{14}$-aryl group; preference is given to the trimethylsilyloxy, triethylsilyloxy, triisopropylsilyloxy, diethylisopropylsilyloxy, dimethylhexylsilyloxy, tert-butyldimethylsilyloxy, tert-butyldiphenylsilyloxy, tribenzylsilyloxy, triphenylsilyloxy and tri-para-xylylsilyloxy groups; particular preference is given to the trimethylsilyloxy group and the tert-butyldimethylsilyloxy group;

z is an integer from 1 to 3;

x is an integer from 0 to 3.

In a particular embodiment, $L^1$ and $L^2$ are joined to one another by one or more covalent bonds. Examples of such ligands are 1,5-cyclooctadienyl ligands ("COD"), 1,6-cyclodecenyl ligands and 1,5,9-all-trans-cyclododecatrienyl ligands.

In a further preferred embodiment, $L^1$ is tetramethylethylenediamine, with only one nitrogen coordinating to the nickel.

When $R^1$ is H, the stereochemistry on the carbon atom bearing $R^1$ can be controlled by the choice of amino acid. L-Amino acids are generally more readily available and for this reason the L configuration on the carbon atom bearing $R^1$ is preferred.

The novel amino acid complexes of the formula I are advantageously prepared by deprotonation of an amino acid of the formula II,

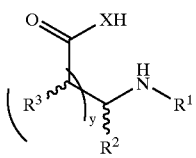

II where the variables are as defined above, by means of a strong base, followed by reaction with a suitable metal compound of the formula $M(L^1)_{z+1}L^2X^1$, where $X^1$ is selected from among halides such as fluoride, chloride, bromide and iodide, preferably fluoride and bromide, and $C_1$–$C_4$-alkoxides such as methoxide, ethoxide and tert-butoxide, and the other variables are as defined above.

Suitable bases are the bases customary in transition metal chemistry, for example lithium diisopropylamide "LDA", alkyllithium compounds such as methyllithium and n-butyllithium and also alkoxides such as sodium methoxide, potassium methoxide, sodium ethoxide, potassium ethoxide, sodium isopropoxide or potassium tert-butoxide, with preference being given to alkoxides. These alkoxides are usually used as a solution in the corresponding alcohol, but can also be used as solids. For the deprotonation of the amino acids of the formula II, the solutions of the alkoxides can be used in freshly prepared form or as commercially available solutions. Preference is given to using freshly prepared alkoxide solutions whose concentration is usually determined by titration.

The reaction conditions for the deprotonation are generally not critical; preference is given to reaction temperatures of from –20° C. to +80° C. and reaction times of from 1 to 60 minutes. To overcome the sometimes very low solubility of the amino acids of the formula II, it is necessary to disperse the amino acids well, for which vigorous stirring and use of ultrasound have been found to be useful.

The molar ratio of base to amino acid can be selected within certain limits, with a molar ratio of from 1.1:1 to 1:1.1 having been found to be preferred and equimolar amounts having been found to be particularly preferred.

The deprotonated amino acids can be isolated and stored for a number of months, although attention has to be paid to exclusion of moisture during storage. However, in a preferred embodiment of the process of the present invention, the deprotonated amino acid is not isolated and is processed further in situ.

The deprotonated amino acid is reacted with a metal compound of the formula $M(L^1)_{z+1}L^2X^1$. The reaction conditions for the reaction are generally not critical. Preference is given to reaction temperatures of from –20° C. to +80° C. and reaction times of from 1 minute to 10 hours, particularly preferably from 1 to 5 hours. The order of addition of the reagents can be chosen freely. The molar ratio of metal compound to deprotonated amino acid can be selected within certain limits, with equimolar amounts having been found to be particularly preferred.

The preparation of suitable metal compounds is known in principle; methods of preparation may be found, for example, in S. Y. Desjardins et al., *J. Organomet. Chem.* 1996, 515, 233.

The reaction mixtures are worked up by the operations customary in coordination chemistry, e.g. crystallization, filtration, precipitation, centrifugation or chromatography, preferably using heatable/coolable columns. When selecting purification methods, attention should be paid to ensuring that the equivalent of the ligand $L^1$ split off during the preparation of the novel amino acid complexes of the formula I is removed essentially quantitatively. Removal of salts of $X^1$ formed during the synthesis, for example $LiX^1$, $NaX^1$ or $KX^1$ depending on the base used, is advantageous.

The novel amino acid complexes of the formula I are in many cases obtained as isomer mixtures. Separation of the isomers is possible in some cases. However, it is not necessary to separate the isomers for use in polymerization.

For the complexes of the formula I to be polymerization-active, they can be activated using an activator, which may also be referred to as cocatalyst. The use of an activator is the preferred embodiment of the present invention.

Suitable cocatalysts are aluminum alkyls of the formula $Al(R^k)_3$, lithium alkyls of the formula $LiR^k$ and aluminoxanes, with particular preference being given to aluminum alkyls of the formula $Al(R^k)_3$ and aluminoxanes.

In these compounds, the radicals $R^k$ are identical or different and are each $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl or n-dodecyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl or tert-butyl.

The structure of the aluminoxanes is not known precisely. They are products obtained by careful partial hydrolysis of aluminum alkyls (cf. DE-A 30 07 725). These products are not pure structurally uniform compounds but mixtures of open-chain and cyclic structures of the types IIIa and b.

In the formulae IIIa and b

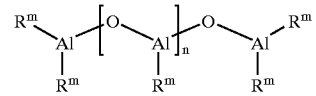

IIIa

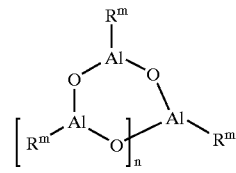

IIIb the radicals $R^m$ are identical or different and are each, independently of one another, $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl, or n-dodecyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably methyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl or cyclododecyl; preferably cyclopentyl, cyclohexyl or cycloheptyl;

$C_7$–$C_{20}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl or 4-phenylbutyl, particularly preferably benzyl, or $C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl, preferably phenyl, 1-naphthyl or 2-naphthyl, particularly preferably phenyl; and n is an integer from 0 to 40, preferably from 0 to 25 and particularly preferably from 0 to 22.

Cage-like structures for aluminoxanes are also discussed in the literature (Y. Koide, S. G. Bott, A. R. Barron *Organometallics* 1996, 15, 2213–26; A. R. Barron *Macromol. Symp.* 1995, 97, 15). Regardless of the actual structure of the aluminoxanes, they are suitable as scavenger alkyls and as cocatalysts for the novel complexes of the formula I. Aluminoxanes are added in significant molar excesses. Thus, a molar ratio M:Al of from 1:5 to 1:5000, preferably from 1:10 to 1:1000 and particularly preferably from 1:50 to 1:500, is chosen.

It is also possible to use mixtures of two or more aluminum alkyls or lithium alkyls as cocatalyst and scavenger alkyl. Mixtures of aluminum alkyls with lithium alkyls are also suitable.

Mixtures of various aluminoxanes are particularly preferred activators in cases where the polymerization is carried out in solution in a paraffin, for example n-heptane or isododecane. A particularly preferred mixture is the CoMAO of the formula $[(CH_3)_{0.9}(iso\text{-}C_4H_9)_{0.1}AlO]_n$ which is commercially available from Witco GmbH.

According to present conceptions, suitable activators for amino acid complexes of the formula I abstract a ligand $L^1$ or $L^2$. In place of aluminoxanes of the formula IIIa or b or the above-described aluminum or boron compounds bearing electron-withdrawing radicals, the activator can be, for example, an olefin complex of rhodium or nickel.

Preferred nickel(olefin)$_a$ complexes, where a=1, 2, 3 or 4, which are commercially available from Aldrich are $Ni(C_2H_4)_3$, $Ni(1,5\text{-cyclooctadiene})_2$ "$Ni(COD)_2$", $Ni(1,6\text{-cyclodecadiene})_2$ or $Ni(1,5,9\text{-all-trans-cyclododecatriene})_2$. Particular preference is given to $Ni(COD)_2$.

Particularly useful activators are mixed ethylene/1,3-dicarbonyl complexes of rhodium, for example, bis(ethylene)rhodium acetylacetonate $Rh(acac)(CH_2=CH_2)_2$, bis(ethylene)rhodium benzoylacetonate $Rh(C_6H_5-CO-CH-CO-CH_3)(CH_2=CH_2)_2$ or $Rh(C_6H_5-CO-CH-CO-C_6H_5)(CH_2=CH_2)_2$. $Rh(acac)(CH_2=CH_2)_2$ is most suitable. This compound can be synthesized as described by R. Cramer in *Inorg. Synth.* 1974, 15, 14.

Some amino acid complexes of the formula I can be activated by means of ethylene. The ease of the activation reaction depends critically on the nature of the ligand $L^1$.

The chosen amino acid complex of the formula I and the activator together form a catalyst system.

The activity of the catalyst system of the present invention can be increased by addition of further aluminum alkyl of the formula $Al(R''')_3$ or aluminoxanes, particularly when compounds of the formula IIa or IIb or the abovementioned aluminum or boron compounds bearing electron-withdrawing radicals are used as activators; aluminum alkyls of the formula $Al(R''')_3$ or aluminoxanes can also act as molar mass regulators. A further effective molar mass regulator is hydrogen. The molar mass can be regulated particularly well via the reaction temperature and the pressure. If the use of a boron compound as described above is desired, the addition of an aluminum alkyl of the formula $Al(R''')_3$ is particularly preferred.

It has been found that the novel amino acid complexes of the formula I are suitable for polymerizing and copolymerizing olefins. They polymerize and copolymerize ethylene and propylene particularly well.

Pressure and temperature conditions during the polymerization can be chosen within wide limits. Pressures in a range from 0.5 bar to 4000 bar have been found to be suitable; preference is given to from 10 to 75 bar or high-pressure conditions from 500 to 2500 bar. As regards the temperature, a range from 0 to 120° C. has been found to be useful; preference is given to from 40 to 100° C., particularly preferably from 50 to 85° C.

Suitable monomers are the following olefins: ethylene, propylene, 1-butene, 1-pentene, 1-hexene, 1-octene, 1-decene or 1-undecene, with particular preference being given to ethylene.

Suitable comonomers are α-olefins, for example from 0.1 to 20 mol % of 1-butene, 1-pentene, 1-hexene, 4-methyl-1-pentene, 1-octene, 1-decene or 1-undecene. Further suitable comonomers are isobutene, styrene and norbornene.

Solvents which have been found to be useful are toluene, ortho-xylene, meta-xylene, para-xylene, ethylbenzene and mixtures of these, also, under high-pressure conditions, supercritical ethylene.

If the use of aluminum alkyl or lithium alkyl as scavenger alkyl proves to be useful, it is advantageous to introduce the aluminum alkyl or lithium alkyl as a solution in a hydrocarbon separately from the catalyst system. However, it is also possible to introduce the scavenger alkyl together with the novel amino acid complexes of the formula I.

The catalyst systems of the present invention have also been found to be hydrogen-regulatable, i.e. the molecular weight of the polymers obtainable by means of the catalyst systems of the present invention can be reduced by addition of hydrogen. If sufficient hydrogen is added, waxes are obtained. The hydrogen concentration required also depends on the type of polymerization plant used. Thus, polyethylene waxes having a molecular weight $M_w$ of at most 20 000 g, preferably at most 10 000 g and particularly preferably at most 7500 g, can be prepared by means of addition of hydrogen when using the complexes of the present invention.

The novel amino acid complexes of the formula I can also be used together with metallocenes for the catalysis of olefin polymerization. For this purpose, they can be activated together with or separately from the metallocenes and can also be introduced into the reactor either together or separately.

If the novel amino acid complexes of the formula I are to be used in polymerization processes such as suspension processes, bulk polymerization processes or gas-phase processes, it is necessary for them to be immobilized on a solid support. Otherwise, polymer morphology problems (lumps, wall deposits, blockages in lines or heat exchangers) can result and force shutdown of the plant. Such an immobilized amino acid complex of the formula I is referred to as catalyst. Preferred catalysts comprise one or more amino acid complexes together with an activator immobilized on a support material.

It has been found that amino acid complexes of the formula I can readily be deposited on a solid support. Possible support materials are, for example, porous metal oxides of metals of groups 2–14 or mixtures thereof, also sheet silicates and zeolites. Preferred examples of metal oxides of groups 2–14 are $SiO_2$, $B_2O_3$, $Al_2O_3$, MgO, CaO and ZnO. Preferred sheet silicates are montmorillonites or bentonites; the preferred zeolite is MCM-41.

Particularly preferred support materials are spherical silica gels and aluminosilicate gels of the formula $SiO_2 \cdot a\, Al_2O_3$, where a is generally in the range from 0 to 2, preferably from 0 to 0.5. Such silica gels are commercially available, e.g. Silica Gel SG 332, Sylopol® 948 or 952 or S 2101 from W. R. Grace or ES 70X from Crosfield.

As particle size of the support material, mean particle diameters of from 1 to 300 μm, preferably from 20 to 80 μm, have been found to be useful; this particle diameter is determined by known methods such as sieve methods. The pore volume of these supports is from 1.0 to 3.0 ml/g, preferably from 1.6 to 2.2 ml/g and particularly preferably from 1.7 to 1.9 ml/g. The BET surface area is from 200 to 750 m²/g, preferably from 250 to 400 m²/g.

To remove impurities, in particular moisture, adhering to the support material, the support materials can be baked before doping, with temperatures of from 45 to 1000° C. being useful. Temperatures of from 100 to 750° C. are particularly suitable for silica gels and other metal oxides. This baking should be carried out for a period of from 0.5 to 24 hours, preferably from 1 to 12 hours. The pressure conditions depend on the method chosen; baking can be carried out in a fixed bed, a stirred vessel or else in a fluidized bed. Baking can quite generally be carried out at atmospheric pressure. However, reduced pressures of from 0.1 to 500 mbar are advantageous; a range from 1 to 100 mbar is particularly advantageous and a range from 2 to 20 mbar is very particularly advantageous. For fluidized-bed methods, on the other hand, it is advisable to operate at slightly superatmospheric pressure in a range from >1 bar to 5 bar, preferably from 1.1 to 1.5 bar.

Chemical pretreatment of the support material with an alkyl compound such as an aluminum alkyl $Al(R''')_3$, a lithium alkyl $LiR^k$ or an aluminoxane of the formula IIa or IIb is also possible.

In the case of a suspension polymerization, use is made of suspension media in which the desired polymer is insoluble or only slightly soluble, since otherwise deposits of the product are formed on parts of the plant in which the product is separated from the suspension medium and force repeated shutdowns and cleaning operations. Examples of suitable suspension media are saturated hydrocarbons such as propane, n-butane, isobutane, n-pentane, isopentane, n-hexane, isohexane and cyclohexane, with preference being given to isobutane.

Pressure and temperature conditions during the polymerization can be chosen within wide limits. A pressure in the range from 0.5 bar to 150 bar has been found to be useful; preference is given to from 10 to 75 bar. A temperature in the range from 0 to 120° C. has been found to be useful; preference is given to from 40 to 100° C., particularly preferably from 50 to 85° C.

Suitable monomers are the following olefins: ethylene, propylene, 1-butene, 1-pentene, 1-hexene, 1-octene, 1-decene and 1-undecene.

Suitable comonomers are α-olefins for example from 0.1 to 20 mol % of 1-butene, 1-pentene, 1-hexene, 4-methyl-1-pentene, 1-octene, 1-decene or 1-undecene. Other suitable comonomers are isobutene, styrene and norbornene.

Furthermore, the catalysts of the present invention have been found to be hydrogen-regulatable, i.e. the molecular weight of the polymers obtainable by means of the catalysts of the present invention can be reduced by addition of hydrogen. If sufficient hydrogen is added, waxes are obtained. The hydrogen concentration required also depends on the type of polymerization plant used. It is also found that the activity of the catalysts of the present invention increases when hydrogen is added.

The catalysts of the present invention can also be used together with one or more other polymerization catalysts known per se. Thus, they can be used together with Ziegler-Natta catalysts, supported metallocene catalysts comprising transition metals of groups 4 to 6 of the Periodic Table of the Elements, catalysts comprising late transition metals (WO 96/23010), Fe or Co complexes with pyridyldiimine ligands, as are disclosed in WO 98/27124, or chromium oxide catalysts of the Phillips type.

It is possible either to mix various catalysts with one another and introduce them into the polymerization vessel together or to use cosupported complexes on a single support or else to introduce various catalysts separately into the polymerization vessel at the same point or at different points.

The polymerization process of the present invention gives polymers, preferably polyethylene, having high molar masses and a low number of branches. The polyethylene obtainable by the process of the present invention is particularly suitable for films.

It has also been found that the novel amino acid complexes of the formula I, in particular those in which M=Ni, are particularly suitable for the polymerization or copolymerization of 1-olefins, preferably ethylene, in emulsion polymerization processes.

Apart from other 1-olefins as comonomers, for example propene, 1-butene, 1-hexene, 1-octene, 1-decene, styrene, norbornene or isobutene, the catalyst system of the present invention also allows the incorporation of polar comonomers, which can be used in amounts of from 0.1 to 50 mol %. Preference is given to acrylates such as acrylic acid, methyl acrylate, ethyl acrylate, 2-ethylhexyl acrylate, n-butyl acrylate or tert-butyl acrylate;

methacrylic acid, methyl methacrylate, ethyl methacrylate, n-butyl methacrylate or tert-butyl methacrylate;

vinyl carboxylates, particularly preferably vinyl acetate;

unsaturated dicarboxylic acids, particularly preferably maleic acid, unsaturated dicarboxylic acid derivatives, particularly preferably maleic anhydride and alkylimides of maleic acid, e.g. N-methylmaleimide.

Furthermore, terpolymers comprising at least 2 of the abovementioned monomers and ethylene can be prepared.

The emulsion polymerization of 1-olefins using the novel amino acid complexes of the formula I can be carried out in a manner known per se.

Here, the order of addition of the reagents in the polymerization is not critical. Thus, the solvent can firstly be pressurized with gaseous monomer or liquid monomer can be metered in, after which the catalyst system is added. However, it is also possible firstly to dilute the solution of the catalyst system with further solvent and subsequently to add the monomer.

The actual polymerization is usually carried out at a minimum pressure of 1 bar; below this pressure the polymerization rate is too low. Preference is given to 2 bar and particular preference is given to a minimum pressure of 10 bar.

The maximum pressure is about 4000 bar; at higher pressures, the demands made of the material of construction of the polymerization reactor are very high and the process becomes uneconomical. Preference is given to 100 bar, particularly preferably 50 bar.

The polymerization temperature can be varied within a wide range. The minimum temperature is about 10° C., since the polymerization rate decreases at low temperatures. Preference is given to a minimum temperature of 40° C., particularly preferably 65° C. The maximum sensible temperature is 350° C., preferably 150° C., particularly preferably 100° C.

Prior to the polymerization, the amino acid complex of the formula I is dissolved in an organic solvent or in water. The solution is stirred or shaken for a number of minutes to ensure that it is clear. The stirring time can be, depending on the solubility of the substance concerned, from 1 to 100 minutes.

At the same time, the activator, if one is necessary, is dissolved in a second portion of the same solvent or in acetone.

Suitable organic solvents are aromatic solvents such as benzene, toluene, ethylbenzene, ortho-xylene, meta-xylene and para-xylene and also mixtures thereof. Further suitable solvents are cyclic ethers such as tetrahydrofuran and dioxane or noncyclic ethers such as diethyl ether, di-n-butyl ether, diisopropyl ether or 1,2-dimethoxyethane. Ketones such as acetone, methyl ethyl ketone or diisobutyl ketone are also suitable, as are amides such as dimethylformamide or dimethylacetamide. It is also possible to use mixtures of these solvents with one another or mixtures of these solvents with water or alcohols such as methanol or ethanol.

Preference is given to using acetone or water or mixtures of acetone and water, with any mixing ratio being able to be employed. The amount of solvent is likewise not critical, but it should be ensured that the amino acid complex and the activator can dissolve completely, otherwise decreases in activity may be expected. The dissolution process can, if desired, be accelerated by ultrasound treatment.

Any emulsifier to be added can be dissolved in a third portion of the solvent or can be dissolved together with the complex.

The amount of emulsifier is selected so that the mass ratio of monomer to emulsifier is greater than 1, preferably greater than 10 and particularly preferably greater than 20. The less emulsifier that has to be used, the better. The activity in the polymerization is significantly increased if an emulsifier is added. This emulsifier can be nonionic or ionic in nature.

Nonionic emulsifiers which can be used are, for example, ethoxylated monoalkylphenols, dialkylphenols and trialkylphenols, (number of EO units: 3 to 50, alkyl radical: $C_4$–$C_{12}$) and ethoxylated fatty alcohols (number of EO units: 3 to 80; alkyl radical: $C_8$–$C_{36}$). Examples are the Lutensol® grades from BASF AG or the Triton® grades from Union Carbide.

Customary anionic emulsifiers are, for example, alkali metal salts and ammonium salts of alkyl sulfates (alkyl radical: $C_8$ to $C_{12}$), of sulfuric monoesters of ethoxylated alkanols (number of EO units: 4 to 30, alkyl radical: $C_{12}$–$C_{18}$) and ethoxylated alkyl phenols (number of EO units: 3 to 50, alkyl radical: $C_4$–$C_{12}$), of alkylsulfonic acids (alkyl radical: $C_{12}$–$C_{18}$) and of alkylarylsulfonic acids (alkyl radical: $C_9$–$C_{18}$).

Suitable cationic emulsifiers are in general primary, secondary, tertiary or quaternary ammonium salts, alkanolammonium salts, pyridinium salts, imidazolinium salts, oxazolinium salts, morpholinium salts, thiazolinium salts bearing a $C_6$–$C_{18}$-alkyl, -aralkyl or heterocyclic radical and also salts of amine oxides, quinolinium salts, isoquinolinium salts, tropylium salts, sulfonium salts and phosphonium salts. Examples which may be mentioned are dodecylammonium acetate or the corresponding hydrochloride, the chlorides or acetates of the various 2-(N,N,N-trimethylammonium)ethylparaffinic esters, N-cetylpyridinium chloride, N-laurylpyridinium sulfate and N-cetyl-N,N,N-trimethylammonium bromide, N-dodecyl-N,N,N-trimethylammonium bromide, N,N-distearyl-N,N-dimethylammonium chloride and the gemini surfactant N,N'-(lauryldimethyl)ethylenediamine dibromide. Numerous further examples may be found in H. Stache, *Tensid-Taschenbuch*, Carl-Hanser-Verlag, Munich, Vienna, 1981 and in McCutcheon's, *Emulsifiers & Detergents*, MC Publishing Company, Glen Rock, 1989.

The components, namely amino acid complex in solution, if desired the solution of an emulsifier and if desired the solution of an activator, are subsequently introduced into the polymerization reactor. Suitable polymerization reactors have been found to be stirred vessels and autoclaves and also tube reactors, with the latter being able to be configured as loop reactors.

The monomer or monomers to be polymerized is/are mixed with the polymerization medium. Polymerization media which can be used are water or mixtures of water with the abovementioned solvents. It has to be ensured that the proportion of water is at least 50% by volume, based on the total mixture., preferably at least 90% by volume and particularly preferably at least 95% by volume.

The solutions of the amino acid complex, if desired an activator and if desired an emulsifier are combined with the mixture of monomer and aqueous polymerization medium. The order of addition of the various components is not critical per se. However, it is necessary that the components are combined sufficiently quickly for no crystallization of any sparingly soluble complexes formed as intermediates to occur.

The process of the present invention gives polyolefins and olefin copolymers in high yields, i.e. the activity of the amino acid complexes of the present invention is very high under the conditions of emulsion polymerization.

As polymerization processes, it is in principle possible to employ continuous and batchwise processes. Preference is given to semicontinuous (semibatch) processes in which all components are mixed and further monomer or monomer mixtures is/are then metered in during the course of the polymerization.

The process of the present invention initially gives aqueous polymer dispersions.

The mean particle diameters of the polymer particles in the dispersions obtained according to the present invention are from 10 to 1000 nm, preferably from 50 to 500 nm and particularly preferably from 70 to 350 nm. The particle diameter distribution does not, however, have to be very uniform. For some applications, particularly for those in which high solids contents (>55%) are employed, broad or bimodal distributions are even preferred.

The polymers obtained by the process of the present invention have industrially interesting properties. In the case of polyethylene, they have a high degree of crystallinity, which can be determined, for example, by the number of branches. Less than 100 branches, preferably less than 50 branches, per 1000 carbon atoms of the polymer are found by means of $^1$H-NMR and $^{13}$C-NMR spectroscopy.

The melting enthalpies of the polyethylenes obtainable by the process of the present invention are greater than 100 J/g, preferably greater than 140 J/g and particularly preferably greater than 180 J/g, measured by DSC.

The molecular weight distributions of the polyethylenes obtainable by the process of the present invention are narrow, i.e. the Q values are in the range from 1.1 to 3.5, preferably from 1.5 to 3.1.

Advantages of the dispersions obtained according to the present invention are the favorable price due to the cheap monomers and process and the fact that they are more stable to weathering than are dispersions of polybutadiene or butadiene copolymers. Compared to dispersions of polymers comprising acrylates or methacrylates as main monomer, the low tendency to saponification is advantageous. A further advantage is that most monomers are volatile and residual, unpolymerized monomers can easily be removed. A final advantage is that no molar mass regulators such as tert-dodecyl mercaptan, which are firstly difficult to separate off and secondly have an unpleasant odor, have to be added during the polymerization.

The polymer particles can be obtained as such from the initially obtained aqueous dispersions by removal of the water and any organic solvent(s). Numerous customary methods are suitable for removing the water and any organic solvent(s), for example filtration, spray drying or evaporation. The polymers obtained in this way have a good morphology and a high bulk density.

The particle diameters can be determined by light scattering methods. An overview may be found in D. Distler "Wäβrige Polymerdispersionen", Wiley-VCH Verlag, 1st Edition, 1999, chapter 4.

The dispersions obtained according to the present invention can be used advantageously in numerous applications, for example paper applications such as paper coating or surface sizing, also paints and varnishes, building chemicals, adhesives raw materials, molded foams, textile and leather applications, carpet backing, mattresses or pharmaceutical applications.

EXAMPLE

General Preliminary Remarks

Abbreviations used: IR spectra: m: medium, s: sharp; NMR spectra: s—singlet, m: multiplet, o-Tol: ortho-tolyl, Ar: aryl, PE: polyethylene, $^t$Bu tert-butyl, THF: tetrahydrofuran, TEA: triethyl aluminum All solvents were dried by standard methods as described, for example, in Organikum, VEB Deutscher Verlag der Wissenschaften, Berlin 1984.

All reactions and purification operations were, unless otherwise indicated, carried out in the absence of air and moisture. The term "ether" always refers to diethyl ether; "pentane" always refers to n-pentane.

The polymer viscosity was determined in accordance with ISO 1628-3. The molar masses were determined by means of GPC. For the GPC analyses, the following conditions based on DIN 55672 were selected: solvent: 1,2,4-trichlorobenzene, flow: 1 ml/min, temperature: 140° C., calibration: PE standards, instrument: Waters 150 C. The number of methyl groups was determined by means of IR spectroscopy.

1. Synthesis of Trans-[Ni(o-Tol)Br(PPh$_3$)$_2$]

The compound trans-[Ni(o-Tol)Br(PPh$_3$)$_2$] was prepared by a slightly modified version of the method of S. Y. Desjardins et al., *J. Organomet. Chem.* 1996, 515, 233.

1.88 g (2.87 mmol) of Ni(PPh$_3$)$_2$Cl$_2$ (commercially available from ABCR GmbH & Co. KG, Karlsruhe) and 1.12 g (17.22 mmol) of Zn powder which had previously been washed with a saturated aqueous NH$_4$Cl solution and then dried at 110° C. were placed in a 100 ml Schlenk flask. 25 ml of THF and 0.69 ml (5.74 mmol) of 2-bromotoluene were subsequently added thereto. The suspension was stirred by means of a precision glass stirrer in an ultrasonic bath for about 35 minutes at 35° C. During this time, the initially greenish black suspension became reddish brown. The residue was subsequently separated off by filtration through Celite® and the filtrate was admixed with about 40 ml of methanol. After a number of hours at −32° C., the product had crystallized out. It was washed with cold methanol.

IR spectrum, $^1$H-NMR spectrum and elemental analysis agreed with the literature data. Further purification was not necessary.

2. Synthesis of the Complexes of the Present Invention 2.1. Synthesis of [Ni(NH$_2$CH$_2$CO$_2$)(o-Tol)(PPh$_3$)]

226.2 mg (0.3 mmol) of trans-[Ni(o-Tol)Br(PPh$_3$)$_2$] were dissolved in 20 ml of THF at room temperature and placed in a Schlenk tube. 22.5 mg (0.3 mmol) of glycine together with 10 ml of methanol were placed in a separate vessel and deprotonated by addition of an equimolar amount of sodium methoxide solution. The suspension obtained in this way was introduced while stirring into the Schlenk tube. After addition of only about half the suspension, the contents of the Schlenk tube became light yellow. The mixture was stirred for a further 2–3 hours at room temperature and the reaction mixture became turbid due to precipitation of NaBr. The precipitate was separated off by centrifugation and the solution was evaporated under reduced pressure. The orange viscous residue which remained was admixed with about 15 ml of diethyl ether and the resulting suspension was stirred for 40 minutes in order to separate off the triphenylphosphine split off in the reaction. The product, which is very sparingly soluble in ether, was centrifuged off and subsequently washed with pentane.

IR (KBr): ν (cm$^{-1}$) 3332 m, 3282 m (NH), 1634 s (COO), 1609 s (NH).

$^1$H-NMR (270 MHz, CD$_3$OD): δ 2.59 (s, 3H, CH$_3$—Ar), 3.19 (m, 2H, NH$_2$), 3.36 (m, 2H, CH$_2$NH$_2$), 6.25–6.28 (m, 4H, aromatic o-Tol.-H), 7.17–7.71 (m, 15H, PPh$_3$).

$^{31}$P-NMR (109.4 MHz, CD$_3$OD): δ 28.36 (s, PPh$_3$).

2.2. Synthesis of [Ni(NH$_2$CHC(CH$_3$)$_3$CO$_2$)(o-Tol)(PPh$_3$)]

350.0 mg (0.46 mmol) of trans-[Ni(o-Tol)Br(PPh$_3$)$_2$] were dissolved in 20 ml of THF at room temperature and placed in a Schlenk tube. 60.3 mg (0.46 mmol) of L-tert-leucine together with 20 ml of methanol were placed in a separate vessel and deprotonated by addition of an equimolar amount of sodium methoxide solution. The suspension obtained in this way was introduced while stirring into the Schlenk tube. After addition of only about 80% by volume of the suspension, the contents of the Schlenk tube became light yellow. The turbidity which occurred as a result of precipitation of NaBr disappeared again on addition of the remaining sodium methoxide. The mixture was stirred for another 3–4 hours at room temperature. The solution was evaporated under reduced pressure. The yellow-orange viscous residue which remained was admixed with about 15 ml of diethyl ether and the resulting suspension was stirred for 40 minutes. The NaBr formed during the reaction was separated off by centrifugation and the product, which was readily soluble in ether, was subsequently isolated as follows: the ether was distilled off under reduced pressure and the light-yellow residue was washed with hexane. This gave the product in analytically pure form. Separation of the N,P isomers was dispensed with.

Although the washings contained some product, no work-up of the washings was carried out.

IR (KBr): ν (cm$^{-1}$) 3435 m (NH), 1637 s (COO), 1601 s (NH).

$^1$H-NMR (270 MHz, CD$_3$OD): δ 1.27 (s, 9H, $^t$Bu), 2.47 (s, CH$_3$—Ar), 2.59 (s, CH$_3$—Ar), 2.98 (s, 1H, CH), 6.35–6.62 (m, 4H, aromatic o-Tol.-H), 7.22–7.73 (m, 15H, PPh$_3$).

$^{31}$P-NMR (109.4 MHz, CD$_3$OD): δ 28.09 (s, PPh$_3$), 28.86 (s, PPh$_3$).

3. Polymerization Examples 60 mg (0.53 mmol) of triethylaluminum (as 2 molar solution in n-heptane, from Witco) and 400 ml of isobutane were placed in a 1 l autoclave. After the autoclave had been pressurized with ethylene to a pressure of 40 bar and had been heated to the temperature indicated in Table 1, the appropriate amount of amino acid complex was in each case added via a lock. After 60 minutes, the polymerizations were stopped by venting.

Data on the polymerization conditions and the product properties may be found in Table 1.

TABLE 1

Polymerization results
[Ni (NH$_2$CH$_2$CO$_2$) (o-Tol) (PPh$_3$)]

| No. | Complex [mg] (μmol) | Cocat. TEA [mg] | PE [g] | T$_{poly}$ [°C.] | H$_2$ [l] | h [dl/g] | M$_v$ [g/mol] | Activity kg of PE/ (mol of Ni · h) | IR-spectroscopic end group analysis | | | |
|---|---|---|---|---|---|---|---|---|---|---|---|---|
| | | | | | | | | | trans-CH=CH—CH$_3$ | Vinyl | Vinylidene | Total CH$_3$ |
| 1 | 20 (41) | 60 | 6 | 100 | — | 9.58 | 900000 | 1756 | 0.20 | 0.20 | 0.05 | 1.80 |
| 2 | 23 (47) | 60 | 3 | 50 | — | 7.97 | 700000 | 766 | 0.19 | 0.69 | 0.11 | 1.40 |
| 3 | 16 (33) | 60 | 5 | 100 | — | 1 | 550000 | 1818 | 0.22 | 0.38 | 0.13 | 3.30 |

η: Staudinger index

We claim:

1. An amino acid complex of the formula I,

I where the variables are defined as follows:

M is selected from the group consisting of Fe, Co, Ni, Pd, Pt and Ir,

X is selected from the group consisting of O and S;

R$^1$ to R$^3$ are identical or different and are each selected from the group consisting of hydrogen, substituted or unsubstituted C$_1$–C$_8$-alkyl, substituted or unsubstituted C$_3$–C$_{12}$-cycloalkyl, C$_7$–C$_{13}$-aralkyl, C$_6$–C$_{14}$-aryl which is unsubstituted or substituted by at least one identical or different substituent selected from the group consisting of C$_1$–C$_8$-alkyl, substituted or unsubstituted, C$_3$–C$_{12}$-cycloalkyl, C$_7$–C$_{13}$-aralkyl, C$_6$–C$_{14}$-aryl, halogen, C$_1$–C$_6$-alkoxy, C$_6$–C$_{14}$-aryloxy, SiR$^4$R$^5$R$^6$ and O—SiR$^4$R$^5$R$^6$, where R$^{4-R6}$ are selected from the group consisting of C$_{1-C8}$-alkyl, C$_3$–C$_{12}$-cycloalkyl, C$_7$–C$_{13}$-aralkyl and C$_6$–C$_{14}$-aryl;

five- to six-membered nitrogen-containing heteroaryl radicals Y, unsubstituted or substituted by at least one identical or different substituent selected from the group consisting of substituted or unsubstituted C$_1$–C$_8$-alkyl, C$_3$–C$_{12}$-cycloalkyl, C$_7$–C$_{13}$-aralkyl, C$_6$–C$_{14}$-aryl, halogen, C$_1$–C$_6$-alkoxy, C$_6$–C$_{14}$-aryloxy, SiR$^4$R$^5$R$^6$ and O—SiR$^4$R$^5$R$^6$, where R$^4$–R$^6$ are selected from the group consisting of C$_1$–C$_8$-alkyl, C$_3$–C$_{12}$-cycloalkyl, C$_7$–C$_{13}$-aralkyl and C$_6$–C$_{14}$-aryl;

and CH$_2$—Y, where R$^1$ and R$^2$ optionally are joined to one another to form a 5- to 10-membered ring;

y is an integer from 0 to 4;

L$^1$ is an uncharged, inorganic or organic ligand selected from the group consisting of phosphines (R$^7$)$_x$PH$_{3-x}$, amines (R$^7$)$_x$NH$_{3-x}$, ethers (R$^7$)$_2$O, H$_2$O, alcohols (R$^7$)OH, pyridine, pyridine derivatives of the formula C$_5$H$_{5-x}$(R$^7$)$_x$N, CO, C$_1$–C$_{12}$-alkyl nitriles and C$_6$–C$_{14}$-aryl nitriles, where x is an integer from 0 to 3;

L$^2$ is an inorganic or organic anionic ligand, where L$^1$ and L$^2$ optionally are joined to one another by one or more covalent bonds, and is selected from the group consisting of halide ions, amide anions (R$^7$)$_h$NH$_{2-h}$, where h is an integer from 0 to 2, C$_1$–C$_6$-alkyl anions, the allyl and methallyl anions, the benzyl anion and C$_6$–C$_{14}$-aryl anions;

R$^7$ are identical or different and are selected from the group consisting of hydrogen, C$_1$–C$_8$-alkyl, C$_3$–C$_{12}$-cycloalkyl, C$_7$–C$_{13}$-aralkyl and substituted or unsubstituted C$_6$–C$_{14}$-aryl;

z is an integer ranging from 1 to 3.

2. The amino acid complex of formula I as claimed in claim 1, wherein

M is selected from the group consisting of Ni and Pd,

X is O, y is 0; and z is1.

3. The amino acid complex of formula I as claimed in claim 1, wherein

M is Ni,

L$^1$ are phosphines (R$^7$)$_x$PH$_{3-x}$, where x=0, 1, 2 or 3,

L$^2$ is a benzyl or aryl anion;

R$^1$ is hydrogen,

R$^7$ are identical or different and are selected from the group consisting of hydrogen hydrogen, C$_1$–C$_8$-alkyl, C$_3$–C$_{12}$-cycloalkyl, C$_7$–C$_{13}$-aralkyl and substituted or unsubstituted C$_6$–C$_{14}$-aryl.

4. An amino acid complex of the formula I,

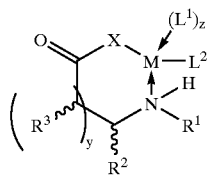

where the variables are defined as follows:

M is Ni,

X is selected from the group consisting of O and S;

$R^1$ to $R^3$ are identical or different and are each selected from the group consisting of hydrogen, substituted or unsubstituted $C_1$–$C_8$-alkyl, substituted or unsubstituted $C_3$–$C_{12}$-cycloalkyl, $C_7$–$C_{13}$-aralkyl, $C_6$–$C_{14}$-aryl which is unsubstituted or substituted by at least one identical or different substituent selected from the group consisting of substituted or unsubstituted $C_1$–$C_8$-alkyl, $C_3$–$C_{12}$-cycloalkyl, $C_7$–$C_{13}$-aralkyl, $C_6$–$C_{14}$-aryl, halogen, $C_1$–$C_6$-alkoxy and $C_6$–$C_{14}$-aryloxy, $SiR^4R^5R^6$ and O—$SiR^4R^5R^6$, where $R^4$–$R^6$ are selected from the group consisting of $C_1$–$C_8$-alkyl, $C_3$–$C_{12}$-cycloalkyl, $C_7$–$C_{13}$-aralkyl and $C_6$–$C_{14}$-aryl;

five- to six-membered nitrogen-containing heteroaryl radicals Y, unsubstituted or substituted by at least one identical or different substituent selected from the group consisting of substituted or unsubstituted $C_1$–$C_8$-alkyl, $C_3$–$C_{12}$-cycloalkyl, $C_7$–$C_{13}$-aralkyl, $C_6$–$C_{14}$-aryl, halogen, $C_1$–$C_6$-alkoxy, $C_6$–$C_{14}$-aryloxy, $SiR^4R^5R^6$ and O—$SiR^4R^5R^6$, where $R^4$–$R^6$ are selected from the group consisting of $C_1$–$C_8$-alkyl, $C_3$–$C_{12}$-cycloalkyl, $C_7$–$C_{13}$-aralkyl and $C_6$–$C_{14}$-aryl;

and $CH_2$—Y, where $R^1$ and $R^2$ optionally are joined to one another to form a 5- to 10-membered ring;

y is an integer from 0 to 4;

$L^1$ is an uncharged, inorganic or organic ligand;

$L^2$ is an inorganic or organic anionic ligand, where $L^1$ and $L^2$ optionally are joined to one another by one or more covalent bonds;

z is an integer ranging from 0 to 3.

5. A process for preparing amino acid complexes as claimed in claim 1, which comprises:
deprotonating an amino acid of formula II

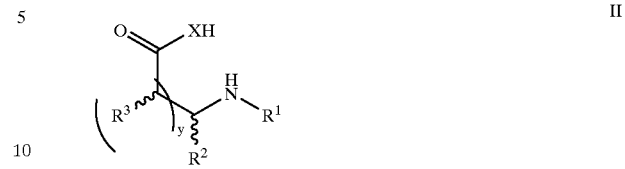

and subsequently reacting the product with a metal compound of the formula $M(L^1)_{2+1}L^2X^1$, where $X^1$ is selected from the group consisting of halides and alkoxides and the other variables are as defined above.

6. The process as claimed in claim 5, wherein the amino acid is deprotonated with a base selected from the group consisting of lithium diisopropylamide, alkyllithium compounds and alkoxides.

7. The process as claimed in claim 5, wherein the deprotonation is conducted at a temperature of −20° C. to 80° C.

8. A process for preparing a supported catalyst for the polymerization or copolymerization of olefins, which comprises:
depositing at least one amino acid complex as claimed in claim 1 and, optionally, an activator on a solid support.

9. The process as claimed in claim 8, wherein the solid support is a porous metal oxide of a metal selected from the group consisting of metals of Groups 2–14, sheet silicates and zeolites.

10. The process as claimed in claim 8, wherein the solid support has a mean particle diameter ranging from 1 to 300 μm and a pore volume ranging from 1.0 to 3.0 ml/g.

11. A supported catalyst for the polymerization or copolymerization of olefins, comprising:
at least one amino acid complex of formula I of claim 1, a solid support material and, optionally, an activator.

12. The supported catalyst as claimed in claim 11, wherein the activator is an aluminum alkyl, an aluminoxane or a boron compound that contains an electron-withdrawing group.

13. A process for the polymerization or copolymerization of olefins, which comprises:
(co)polymerizing at least one monomer olefin in the presence of amino acid complex as claimed in claim 1.

14. The process as claimed in claim 13, wherein said olefin is ethylene, propylene, 1-butene, 1-pentene, 1-hexene, 1-octene, 1-decene or 1-undecene.

15. The process as claimed in claim 13, wherein the (co)polymerization is conducted in the presence of from 0.1 to 20 mol % of a comonomer that is isobutene, styrene, norbornene, 1-butene, 1-pentene, 1-hexene, 4-methyl-1-pentene, 1-octene, 1-decene or 1-undecene.

16. The process as claimed in claim 15, wherein the (co)polymerization is conducted in the presence of the supported catalyst as claimed in claim 11.

17. The process as claimed in claim 15, wherein the (co)polymerization is conducted as an emulsion polymerization process or an emulsion copolymerization process.

* * * * *